United States Patent [19]

Grivas et al.

[11] Patent Number: 4,457,806
[45] Date of Patent: Jul. 3, 1984

[54] PROCESS FOR VINYL AROMATIC MONOMER POLYMERIZATION INHIBITION

[75] Inventors: John C. Grivas, Oak Lawn; Myong-Gi A. Park, Dolton, both of Ill.

[73] Assignee: The Sherwin-Williams Company, Cleveland, Ohio

[21] Appl. No.: 393,005

[22] Filed: Jun. 28, 1982

[51] Int. Cl.³ .......................... B01D 3/34; C07C 7/05; C07C 7/20
[52] U.S. Cl. .......................................... 203/9; 203/65; 585/4; 585/860
[58] Field of Search .......................... 203/9, 8, 65, 6, 7; 208/48 AA; 585/1–5, 800, 860

[56] References Cited

U.S. PATENT DOCUMENTS

| | | | |
|---|---|---|---|
| 2,526,567 | 10/1950 | Drake et al. | 203/9 |
| 4,033,829 | 7/1977 | Higgins et al. | 203/9 |
| 4,105,506 | 8/1978 | Watson | 203/9 |
| 4,182,658 | 1/1980 | Watson | 203/9 |
| 4,252,615 | 2/1981 | Watson | 203/9 |

*Primary Examiner*—Wilbur L. Bascomb, Jr.
*Attorney, Agent, or Firm*—James V. Tura; Robert E. McDonald

[57] ABSTRACT

This invention is directed to the use of a polymerization inhibitor in the distillation of readily polymerizable vinyl aromatic monomers and more specifically to the use of mixtures of 2,6-dinitro-4-ethyl-phenol as a polymerization inhibitor for vinyl aromatic monomers such as styrene and vinyl benzenes. The invention comprises the process of subjecting the vinyl aromatic monomers to distillation temperatures in the presence of mixtures of 2,6-dinitro-4-ethyl-phenol and 2,6-dinitro-paracresol to prevent polymerization.

10 Claims, No Drawings

PROCESS FOR VINYL AROMATIC MONOMER POLYMERIZATION INHIBITION

BACKGROUND OF THE INVENTION

This invention is directed to a process for the distillation or readily polymerizable vinyl aromatic compounds or monomers such as styrene, substituted styrene and vinyl benzenes and more specifically to a process for the distillation of vinyl aromatic monomers wherein the degree of polymerization of the monomer is substantially reduced under distillation conditions by the presence of small but effective amounts of a mixture of two inhibitors.

It is generally known that vinyl aromatic compounds such as monomeric styrene and the alkylated styrenes such as methyl styrene, ethyl styrene, etc. are easily polymerized under distillation conditions and more particularly the rate of polymerization of the monomers increase substantially at increased temperatures. Many vinyl aromatic monomers available commercially, generally contain a variety of impurities and therefore these monomers must be purified, i.e. by distillation under a reduced pressure, to obtain the substantially pure monomer, i.e. styrene, for industrial use. As indicated, the purification and separation of these impurities from the monomers is generally accomplished by distillation. Thus, in order to prevent polymerization of the monomers during the distillation purification process, various inhibitors are added to the distillation as polymerization inhibitors.

For example, sulfur has been employed as a polymerization inhibitor. However, sulfur while being a reasonable effective inhibitor, its use has many disadvantages in that the waste materials formed are highly contaminated with sulfur and therefore represent a serious pollution and waste removal problem. Other inhibitors include alkylated catechol, hydroquinone, and a number of the halogen-substituted cresols such as 2-chloro-6-nitro-paracresol, 2-bromo-6-nitro-paracresol and mixtures of these materials as specifically taught in U.S. Pat. No. 4,132,602. In addition, other inhibitors include 3-nitro-2,5-cresotic acid and 3-nitro-2,5-cresotaldehyde as taught in U.S. Pat. No. 4,132,601. Still further, other known vinyl inhibitors include the halogenated toluenes such as 4-halo-3,5-dinitrotoluene as taught in U.S. Pat. No. 4,132,603 and the nitro cresols as taught in U.S. Pat. No. 4,086,147.

While some of these compounds are effective for inhibiting the polymerization of vinyl aromatic compounds, not all of the compounds have been totally successful as polymerization inhibitors under the stringent conditions of distillation. It was found that notwithstanding the use of these inhibitors, the distillation of crude styrene, for example, resulted in products containing substantial quantities of polymer which is difficult to separate from the monomer.

More important, a number of the known vinyl aromatic inhibitors have high melting points such as dinitro paracresol with a melting point of about 85° C. and therefore is transported as a solid. Thus, before using dinitro paracresol, it must be dissolved in a solvent, e.g. ethyl benzene which subsequently requires separation. This requires additional equipment and adds to the process time and cost. Moreover, it is necessary to add the inhibitor as a solution of ethyl benzene to the monomer, e.g. styrene, since dinitro paracresol can not be held at temperatures greater than 85° C. for any period of time due to the potential danger of side reactions and because of the explosive nature of the compound.

In comparison, the 2,6-dinitro-4-ethylphenol

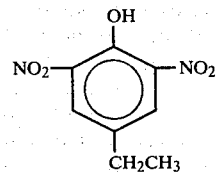

STRUCTURE I of this invention has a melting point of about 36° C. and therefore can be transported in the liquid form, e.g. at temperatures ranging from 38° to 48° C. and metered directly into the distillation process, i.e. distillation of styrene, requiring no separation or other equipment. Moreover, it was found that mixtures of 2,6-dinitro-4-ethylphenol with other inhibitors, i.e. 2,6-dinitro-paracresol are liquid at about room temperature and therefore easy to handle and substantially less costly to use. For example, a mixture of 2,6-dinitro-paracresol with 2,6-dinitro-4-ethylphenol at a ratio of 1:3 was found to have a freezing point of about 5° C. and the any danger of side reactions in minimal.

Accordingly, it is an object of this invention to provide a polymerization inhibitor useful for distillation of vinyl aromatic compounds particularly styrene, and vinyl benzenes at elevated temperatures, under a vacuum, which is easy to use and handle and has a minimum possibility of side reactions. It is another object of this invention to provide a polymerization inhibitor for styrene and vinyl benzenes which is liquid at ambient temperatures and can be added directly to the distillation process without any prior treatment or handling.

These and other objects of the invention will become apparent from a further and more detailed description of the invention as follows. Specifically, this invention relates to a process for distilling polymerizable vinyl aromatic monomers such as styrene, substituted styrenes, alkyl benzenes and the like by subjecting the vinyl aromatic monomers to distillation temperatures under a reduced pressure in the presence of small but effective amounts of mixtures of 2,6-dinitro-4-ethylphenol and 2,6-dinitro-paracresol. The dinitro-4-ethylphenol is present in the mixture in amounts ranging from about 1% to 99% by weight of the mixture.

Generally, the process of distillation is carried out in the presence of effective amounts of the polymerization inhibitor which ranges from about 50 to 3,000 parts by weight of the inhibitor per million parts by weight of the vinyl aromatic monomer and preferrably in amounts ranging from about 100 to 1,000 parts per million parts by weight of the vinyl monomer. The temperatures at which the distillation is generally carried out ranges from about 40° C. to 160° C. and depending on the particular monomer being distilled and the temperatures utilized the amount of inhibitor added to the system will vary within the range herein stated.

With some monomers it is desirable to use mixtures of 2,6-dinitro-4-ethylphenol and 2,6-dinitro-paracresol wherein the dinitro-4-ethylphenol is present in amounts ranging from about 1% to 99% by weight of the mixture. The mixture may be added to the distillation of the monomer in amounts ranging from about 100 to 1,000 parts per million parts by weight of the vinyl aromatic monomer. As stated, 2,6-dinitro-4-ethylphenol has a melting point of about 36° C. and can be transported in the liquid form, i.e. at temperatures ranging from about 38° to 40° C. and metered directly into the distillation. It was found also that mixtures of 2,6-dinitro-4-ethylphenol and 2,6-dinitro-paracresol are liquid at ambient temperatures and can be metered into the distillation in the same manner as 2,6-dinitro-4-ethylphenol alone. More specifically, a mixture of 2,6-dinitro-paracresol and 2,6-dinitro-4-ethylphenol in a ratio of 1 to 3 has a freezing point of about 5° C. and can be metered into the distillation process as a liquid without concern of any side reactions.

SPECIFIC EMBODIMENTS

Freshly distilled styrene, free of tertiary butyl catechol, was placed in a round bottom flask equiped with a magnetic bar. Specific amounts of 2,6-dinitro-4-ethylphenol, 2,6-dinitro-paracresol and mixtures of 2,6-dinitro-4-ethylphenol and 2,6-dinitro-paracresol were added to the reactor with stirring. The reactor was closed and placed in a preheated oil bath held at 115°±1° C. and stirred for about four hours. A sample was withdrawn from the reactor, weighed and the amount of polymer formed was precipitated by the addition of absolute methanol (25 mls per 5 g of samples). The precipitate was filtered off, washed with cold methanol and dried. The degree of polymerization (compared with 2,6-dinitro-paracresol) is shown in Table I. The melting points of the pure compounds and mixtures thereof are shown in Table II.

TABLE I

Polymerization of styrene at 115 ± 1° C. in the presence of DNPEP, DNPC and mixtures thereof (After 4 hours)

| | DNPEP ppm | DNPC ppm | Polymerization % |
|---|---|---|---|
| 1. | 100 | — | 18.5 |
| 2. | — | 100 | 14.8 |
| 3. | 50 | 50 | 15.2 |
| 4. | 75 | 25 | 15.3 |
| 5. | 200 | — | 4.9 |
| 6. | — | 200 | 2.6 |
| 7. | 100 | 100 | 4.9 |
| 8. | 150 | 50 | 3.5 |
| 9. | 300 | — | 3.6 |
| 10. | — | 300 | 2.5 |
| 11 | 150 | 150 | 2.6 |
| 12. | 225 | 75 | 2.1 |
| 13. | 400 | — | 2.2 |
| 14. | — | 400 | 2.2 |
| 15. | 200 | 200 | 1.9 |
| 16. | 300 | 100 | 1.8 |
| 17. | 1000 | — | 1.1 |
| 18. | — | 1000 | 1.1 |

DNPEP is 2,6-dinitro-4-ethylphenol
DNPC is 2,6-dinitro-paracresol

TABLE II

Freezing Points of DNPEP/DNPC Mixture

| DNPEP | DNPC | FP °C. |
|---|---|---|
| 100% | — | 36 |
| 90 | 10 | 6 |
| 80 | 20 | 7 |
| 75 | 25 | 5 |
| 70 | 30 | 11 |
| 60 | 40 | 17 |
| 50 | 50 | 26 |
| 40 | 60 | 39 |
| — | 100 | 85 |

As noted from the data in Table I, as the amount of dinitro-para-ethylphenol increased to 1,000 parts per million, the percent of polymerization of the styrene dropped to 1.1%. Similarly, as the parts per million of the 2,6,-dinitro-4-ethylphenol mixture was increased from 100 to 1,000, the percent of polymerization decreased from 18.5% to 1.1%. Further, the data in Table II illustrates that the freezing point of 2,6-dinitro-paracresol has a freezing point of 85° C. and that 2,6-dinitro-4-ethylphenol has a freezing point of only 36° C., however, a mixture of these two inhibitors, i.e. the ethylphenol and paracresol has freezing points ranging from 5° to 39° C. depending on the ratio of the mixture.

It is obvious from the data in the Tables that as the percent of the dinitro-4-ethylphenol ranges from 40 to 100% of the mixture or if used alone, the freezing points of the mixture do not exceed 39° C. and may be as low as 5° C. Therefore, 2,6-dinitro-4-ethylphenol alone can be added as a liquid to the distillation process or mixtures of 2,6-dinitro-4-ethylphenol with 2,6-dinitro-paracresol, wherein the ethylphenol is present in the mixture in amounts at least 40% can be added as a liquid since the freezing point is below 39° C.

It is evident from the data set forth that the addition of 2,6-dinitro-4-ethylphenol alone or in combination with 2,6-dinitro-paracresol to the distillation of vinyl aromatic compounds not only improves the mechanism for adding the inhibitors but also substantially decreases the rate of polymerization of the monomer as compared to other known inhibitors.

While this invention has been described by a number of specific embodiments, it is obvious that there are other modifications which can be made without departing from the spirit and scope of the invention as set forth in the appended claims.

The invention claimed is:

1. A process for distilling a polymerizable vinyl aromatic monomer which comprises subjecting the vinyl aromatic monomer to distillation temperatures in the presence of effective amounts of polymerization inhibitors consisting of mixtures of 2,6-dinitro-4-ethylphenol and 2,6-dinitro-paracresol; wherein the dinitro-4-ethylphenol is present in amounts ranging from about 1% to 99% by weight of the mixture.

2. The process of claim 1 further characterized in that the vinyl aromatic monomer is styrene.

3. The process of claim 1 further characterized in that the vinyl aromatic monomer is an alkyl substituted styrene.

4. The process of claim 1 further characterized in that an effective amount of the polymerization inhibitor ranges from about 50 to 3,000 parts per million parts by weight of the vinyl aromatic monomer.

5. The process of claim 1 further characterized in that the distillation temperatures range from about 40° to 160° C.

6. The process of claim 1 further characterized in that the inhibitor is a mixture of 2,6-dinitro-4-ethylphenol and 2,6-dinitro-paracresol, wherein the dinitro-4-ethylphenol is present in amounts ranging from about 40 to 90% by weight of the mixture; and said mixture being present in amounts ranging from about 100 to 1000 parts per million parts by weight of the vinyl aromatic monomer.

7. A process for inhibiting the polymerization of polymerizable vinyl aromatic monomers which comprises subjecting said vinyl aromatic monomers to distillation temperatures in the presence of about 100 to 1,000 parts by weight, per million parts of monomers, of polymerization inhibitors consisting of a mixture of 2,6-dinitro-4-ethylphenol and 2,6-dinitro-paracresol; wherein said 2,6-dinitro-4-ethylphenol is present in an amount ranging from about 1% to 99% by weight of the mixture.

8. The process of claim 7 further characterized in that the the distillation temperatures of the vinyl aromatic monomers range from about 40° to 160° C.

9. The process of claim 7 further characterized in that the vinyl aromatic monomer is styrene.

10. The process of claim 7 further characterized in that the inhibitor is a mixture of one to three parts of 2,6-dinitro-4-ethylphenol and one part of 2,6-dinitro-paracresol.

* * * * *